(12) United States Patent
Cogels et al.

(10) Patent No.: US 8,779,135 B2
(45) Date of Patent: Jul. 15, 2014

(54) METHOD FOR THE MANUFACTURE OF AMINOHYDROXY DIPHOSPHONIC ACIDS

(75) Inventors: Samuel Corentin Cogels, Ixelles (BE); David Lemin, Watermael-Boitsfort (BE); Patrick Notté, Wavre (BE)

(73) Assignee: Straitmark Holding AG, Zug (CH)

( * ) Notice: Subject to any disclaimer, the term of this patent is extended or adjusted under 35 U.S.C. 154(b) by 0 days.

(21) Appl. No.: 13/498,814

(22) PCT Filed: Oct. 4, 2010

(86) PCT No.: PCT/EP2010/064755
§ 371 (c)(1),
(2), (4) Date: Jun. 12, 2012

(87) PCT Pub. No.: WO2011/039378
PCT Pub. Date: Apr. 7, 2011

(65) Prior Publication Data
US 2012/0245354 A1 Sep. 27, 2012

(30) Foreign Application Priority Data

Oct. 2, 2009 (EP) .................................... 09172040

(51) Int. Cl.
| C07F 9/38 | (2006.01) |
|---|---|
| C07F 9/572 | (2006.01) |
| C07F 9/58 | (2006.01) |
| C07F 9/59 | (2006.01) |
| C07F 9/6506 | (2006.01) |
| C07F 9/6561 | (2006.01) |

(52) U.S. Cl.
USPC ............... 546/23; 546/22; 548/112; 548/415; 562/13

(58) Field of Classification Search
None
See application file for complete search history.

(56) References Cited

U.S. PATENT DOCUMENTS

| 4,407,761 | A | 10/1983 | Blum et al. |
|---|---|---|---|
| 5,019,651 | A | 5/1991 | Kieczykowski |
| 5,648,491 | A | 7/1997 | Dauer et al. |
| 5,908,959 | A | 6/1999 | Kubela et al. |
| 6,573,401 | B1 | 6/2003 | Boschi Llado et al. |
| 2001/0041690 | A1 | 11/2001 | Caser et al. |

FOREIGN PATENT DOCUMENTS

| DE | 222030 A1 | 5/1985 |
|---|---|---|
| DE | 235068 A1 | 4/1986 |
| WO | 2004/067541 A1 | 8/2004 |
| WO | 2009/068636 A1 | 6/2009 |

OTHER PUBLICATIONS

Kieczykowski G. R.: "Preparation of (4-amino-1-hydroxybutylidene) bisphosphonic acid sodium salt, MK217 (Alendronate Sodium). An Improved Procedure for the Preparation of 1-Hydroxy-1, 1,-Bisphosphonic Acids", Journal of Organic Chemistry, American Chemical Society, Easton.: US, vol. 60, No. 25, Jan. 1, 1995, pp. 8310-8312.
Schuelke U.: "Phosphonylation by Tetraphosphorus Hexoxide", Phosphorus, Sulfur and Silicon and the Related Elements, Gordon and Breach Science Publishers, Amsterdam, GB, vol. 51/52, Jan. 1, 1990, pp. 153-156.

*Primary Examiner* — Janet L Andres
*Assistant Examiner* — Timothy R Rozof
(74) *Attorney, Agent, or Firm* — Husch Blackwell LLP; Samuel Digirolamo

(57) ABSTRACT

The technology of this invention concerns a method for the manufacture of hydroxy diphosphonic acids containing an amino moiety. The method specifically involves reacting a liquid $P_4O_6$ with an aminocarboxylic acid in the presence of a sulfonic acid. The aminocarboxylic acid is selected from 3 structurally different compounds. The amino hydroxy diphosphonic acids can be synthesized with high selectivity and purity and the unreacted starting raw materials can easily and conveniently be recirculated.

13 Claims, No Drawings

METHOD FOR THE MANUFACTURE OF AMINOHYDROXY DIPHOSPHONIC ACIDS

CROSS REFERENCE TO RELATED APPLICATIONS

This application is a U.S. National Phase patent application of International Application PCT/EP2010/064755, filed 4 Oct. 2010, which claims the benefit of priority from European Patent Application No. 09172040.9 filed on 2 Oct. 2009. The disclosures of International Application PCT Application No. PCT/EP2010/064755 and European Patent Application No. 09172040.9 are incorporated herein by reference.

This invention pertains to a method for the manufacture of hydroxy diphosphonic acids containing an amino moiety. The method specifically contemplates reacting a liquid $P_4O_6$ with an aminocarboxylic acid and a selected sulfonic acid whereby, in particular executions, the liquid $P_4O_6$ is added to the solution of the aminocarboxylic acid in the sulfonic acid or the liquid $P_4O_6$ is added to the sulfonic acid followed by the addition of the aminocarboxylic acid. The aminocarboxylic acid can be selected from a group of 3 different compounds exhibiting narrowly defined structural features. The reaction is conducted by heating the reaction mixture at a temperature in the range of from 40° C. to 180° C. for a duration of from 10 minutes to 30 hours followed by recovering the reaction product formed in an appropriate manner.

The prior art relating to the manufacture of amino hydroxydiphosphonic acids generally is very crowded representing several decennia of intense R&D efforts. Aminohydroxy diphosphonic acids can be used in a variety of established applications including sequestrant, chelant, water-treatment, detergent, corrosion and in pharmaceutical applications including osteoporosis and other bone treatment conditions. The conventional manufacture of bisphosphorylation products is based on using combinations of phosphorous acid and phosphorus halides. This technology is described in a large series of documents, leading examples of which state of the art are briefly summarized. U.S. Pat. No. 5,908,959 pertains to a method for the production of aminohydroxy butylidene bisphosphonic acid wherein the corresponding aminocarboxylic acid is reacted with a mixture of phosphorous acid and phosphorus trichloride in a solution of polyalkylene glycol. U.S. Pat. No. 5,648,491 also concerns a process for producing aminohydroxy butylidene bisphosphonic acid. In detail, the aminoalkane carboxylic acid is continuously mixed with phosphorous acid and phosphorus trichloride in methane sulfonic acid whereby an aqueous base is continuously added to the overflow mixture, containing intermediate products, followed by hydrolyzing the overflow mixture and recovering the bisphosphonic acid formed. US 2001/0041690 divulges a process for making bisphosphonates with high yields and little residual elemental phosphorus by-products. The process actually requires the use of molten phosphorous acid, an aminocarboxylic acid, phosphorus trihalide and a base. The amount of phosphorus trihalide in relation to the aminocarboxylic acid is about 2 equivalents. The phosphorous acid and the base act as a solvent to yield a uniform reaction mixture or solution. U.S. Pat. No. 4,407,761 describes a process for the making of aminohydroxyalkylidene bisphosphonic acid by reacting an aminocarboxylic acid with a phosphonating reactant consisting of a mixture of phosphorous acid and phosphorus trichloride/oxychloride, followed by hydrolyzing the reaction mixture with concentrated hydrochloric acid and recovering the bisphosphonic acid formed.

U.S. Pat. No. 5,019,651 concerns a method for the preparation of aminohydroxy butylidene bisphosphonic acid whereby an aminocarboxylic acid is reacted with a mixture of phosphorous acid and phosphorus trichloride in the presence of methane sulfonic acid followed by contacting the reaction mixture so obtained with a hydrolysis mixture, possibly a phosphate buffer, thereby maintaining the pH between 4-10 and recovering the end product.

U.S. Pat. No. 6,573,401 discloses a process for producing amino 1-hydroxybutylidene-1,1-diphosphonic acid, and the trihydrated monosodium salt thereof by using a phosphonation mixture of phosphorous acid/methanesulfonic acid anhydride in molar ratios of 2:5 to 5:2, preferably 1:1. The aminobutyric acid and the phosphonation acid are used in molar ratios, butyric acid:phosphorous acid of 2:1 to 5:1, preferably 3:1. The trihydrated monosodium salt can be filtered before being converted into the phosphoric acid. The technology is said to allow the synthesis to proceed homogeneously without the reaction mixture solidifying. In addition, the reaction does not require the use of hazardous phosphorus chloride starting products.

DD 235068 relates to a process for the manufacture of amino-hydroxydiphosphonic acid starting from an amino carboxylic acid, phosphoric acid and $P_4O_6$ in molar ratios: carboxylic acid:$H_3PO_4$:$P_4O_6$ of from 3:10:1 to 1:0.1:1, preferably 2:2:1. DD 222030 also pertains to a method for preparing amino-hydroxy diphosphonic acids starting from the corresponding aminocarboxylic acid and $P_4O_6$ in an inert solvent, e.g. dioxane.

The various prior art technologies, taken singly or combined, do not provide a viable solution to the established aminohydroxy diphosphonic acid manufacturing insufficiencies and shortcomings. The manufacturing requirements basically hinge around selectivity and/or yield and/or purity and/or efficiency in addition to environmental constraints and the need for a manufacturing arrangement which allows an easy recycling of all reaction partners, in particular unreacted raw materials. In particular, the art reaction systems are mostly conducted in the presence of phosphorus halides which, while known to create significant difficulties are frequently accepted. A number of art technologies acknowledge the formation of orange-yellow colored by-products, associated with LOOPS (low oxides of phosphorus), which by-products can represent safety and operational hazards.

It is therefore a major object of this invention to provide a method for the manufacture of aminohydroxy diphosphonic acids capable of synthesizing substantially stoichiometric proportions of the diphosphonic acid starting from essentially stoichiometric proportions of the essential starting materials. It is another object of this invention to generate an improved method for making aminohydroxy diphosphonic acids with outstanding selectivity and high yields. Another important object of the invention contemplates producing very pure aminohydroxy diphosphonic acids under substantial exclusion of LOOPS. Yet another object aims at providing a process for the beneficial and convenient recycling of unreacted reaction partners. Still another object contemplates providing manufacturing technology capable of yielding diphosphonic acids of high purity requiring minimal/reduced purification treatment for in that respect demanding applications, including pharmaceutical and quasi-pharmaceutical applications. One particularly important object of the invention aims at providing a method for the economic manufacturing of selected aminohydroxy diphosphonic acids in high yields and purity in a one step processing arrangement, to wit:

3-(dimethylamino)-1-hydroxypropylidene-1,1-bisphosphonic acid, also known as olpadronic acid;

phosphonic acid, (1-hydroxy-2-imidazo[1,2-a]pyridine-3-yl-ethylidene)bis-, also known as minodronic acid;

1-hydroxy-2-(3-pyridinyl)ethylidene bisphosphonic acid, also known as risedronic acid;

(3-amino-1-hydroxypropylidene)-1,1-bisphosphonic acid, also known as pamidronic acid;

6-amino-1-hydroxyhexane-1,1-diphosphonic acid, also known as neridronic acid;

[1-hydroxy-3-(methylpentylamino)propylidene]diphosphonic acid, also known as ibandronic acid;

4-amino-1-hydroxybutane-1,1-diphosphonic acid, also known as alendronic acid, and 2-(imidazol-1-yl)-1-hydroxy-1,1'-ethylidenediphosphonic acid, also known as zoledronic acid.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions. The term "LOOPS" means "low oxides of phosphorus". The term "aminohydroxy diphosphonic acids" embraces 1-hydroxy-1,1-bisphosphonic acids containing, at least, one nitrogen atom as further defined in this application document. The terms "cyclic; aromatic; heterocyclic; and heteroaromatic" can embrace "polycyclic; polyaromatic; heteropolycyclic; and heteropolyaromatic" structures and will have that meaning unless defined differently. Heteropolycyclics and heteropolyaromatics embrace polycyclic and polyaromatic species wherein at least one cycle contains at least one heteroatom selected from nitrogen, oxygen and sulphur. The term "% w/w" as used in the Examples refers to P derivatives as detected by $^{31}P$ NMR. The term "liquid $P_4O_6$" embraces neat $P_4O_6$ in the liquid state, solutions of $P_4O_6$ in a suitable solvent, solid $P_4O_6$ and gaseous $P_4O_6$.

The foregoing and other objects can now be achieved by using a method of manufacturing whereby a liquid $P_4O_6$ and an aminocarboxylic acid are reacted in the presence of a sulfonic acid under narrowly defined conditions. In more detail, the method for the manufacture of an aminohydroxy diphosphonic acid starting from the corresponding aminocarboxylic acid, liquid $P_4O_6$ and a sulfonic acid comprises the steps as follows:

a: adding the liquid $P_4O_6$ to the solution of the aminocarboxylic acid in the sulfonic acid; or b: adding the liquid $P_4O_6$ to the sulfonic acid followed by the addition of the aminocarboxylic acid;

wherein the sulfonic acid is selected from homogeneous and heterogeneous sulfonic and polysulfonic acids; and the aminocarboxylic acid and the $P_4O_6$ are used in molar ratios of from 4:1 to 1:1 and the sulfonic acid is used in a level of from 1 to 30, preferably 3 to 20, in particular 6 to 18, equivalents per mol of aminocarboxylic acid; and wherein the aminocarboxylic acid is selected from the group of:

$$(A)(B)N—X^1—COOH \qquad \text{i}$$

wherein $X^1$ is such that there are at least two carbon units between COOH and N; $X^1$ can be represented by a hydrocarbon group selected from linear, branched, cyclic and aromatic species having from 2 to 20 carbon atoms, optionally substituted by one or more groups selected from $CF_3$, F, Cl, SR, $NR'_2$, $SO_2R$ and OR; A and B are independently selected from H, hydrocarbon groups having from 1 to 20 carbon atoms in branched, linear, cyclic, aromatic, heterocyclic or hetero aromatic configuration which can be substituted by OR, SR, $CF_3$, F, Cl, $NR'_2$, $SO_2R$ and/or R wherein R represents an alkyl group having from 1 to 12 carbon atoms in linear, branched, cyclic, aromatic, heterocyclic or heteroaromatic configuration which can be substituted by OR", SR", $CF_3$, F, Cl, $NR'''_2$ and/or $SO_2R''$ wherein R' is selected from R and hydrogen and can be selected independently; R" represents a hydrocarbon group having from 1 to 12 carbon atoms in linear, branched, cyclic, aromatic, heterocyclic or heteroaromatic configuration; R''' is selected from R" and hydrogen and R''' groups can be chosen independently; wherein the heterocyclic and heteroaromatic groups can contain from 1 to heteroatoms independently selected from nitrogen, sulphur and oxygen; such that the difference between the number of member atoms in the individual cycles of these heterocyclic or heteroaromatic rings minus the number of heteroatoms in the individual cycles of these heterocyclic or heteroaromatic rings is at least 2; provided that the carbon atom next to the carboxylic acid group is solely connected to hydrogen and, at least, one carbon atom which carries the N(A) (B) group; when A is H, B can also be a COOT group whereby T is a $C_1$-$C_{10}$ alkyl group or a $C_6$-$C_{10}$ aromatic moiety;

$$D—X^2—COOH \qquad \text{ii}$$

wherein $X^2$ is at least one carbon atom between COOH and N; $X^2$ is a hydrocarbon group in linear, branched, cyclic or aromatic configuration having from 1 to 20 carbon atoms in said group, optionally substituted by $CF_3$, F, Cl, $NR'_2$, SR, $SO_2R$ and/or OR; with the proviso that when there is only one carbon atom between COOH and N then D represents a heteromonoaromatic group, it is understood that the heteromonoaromatic and heteromonocyclic groups contain at least one nitrogen atom, in all other cases D represents a heteromonocyclic or heteromonoaromatic group containing at least one nitrogen atom directly attached to $X^2$, said heteromonocyclic cycle or heteromonoaromatic cycle being represented by a 4 to 8 member ring and containing from 1 to additional hetero atoms chosen from nitrogen, oxygen and sulphur which cycle can be optionally substituted by one or more groups selected from $CF_3$, F, Cl, $NR'_2$, SR, $SO_2R$ and OR, which heteromonocycle or heteromonoaromatic cycle can be further substituted by one or more $C_1$-$C_{10}$ linear, branched cyclic, aromatic, heterocyclic or heteroaromatic moieties, which can be substituted by one or more groups selected from $CF_3$, F, Cl, $NR'''_2$, SR", $SO_2R''$ and OR", wherein R, R', R" and R''' have the meaning recited above; which cyclic, heterocyclic, aromatic or heteroaromatic moieties, containing from 1 to 4 heteroatoms chosen from nitrogen, oxygen and sulphur, can be fused onto the D group or attached to the D group by a single bond whereby in the cyclic structure fused onto the D group not more than four individual cycles are present; whereby the heterocyclic and heteroaromatic moieties, fused onto or attached to the D group by a single bond, and the D group itself, are such that the difference between the number of member atoms in the individual cycles of these heterocyclic or heteroaromatic rings minus the number of heteroatoms in the individual cycles of these heterocyclic or heteroaromatic rings is at least 2; whereby the D group can also be represented by an imide derived from the $NH_2$ group attached to the $X^2$ moiety, formed by reaction with a cyclic anhydride; provided that the carbon atom next to the carboxylic acid group in ii is solely connected to hydrogen and, at least, one carbon atom which carries the D group and, when in ii, $X^2$ is solely a one carbon unit between COOH and N in D, then that carbon atom can be solely substituted by hydrogen and carbon atoms and $$E—X^3—COOH \qquad \text{iii}$$

wherein $X^3$ is a direct link or a $C_1$-$C_{20}$ linear, branched, cyclic or aromatic hydrocarbon group, optionally substituted by $CF_3$, F, Cl, $NR'_2$, SR, $SO_2R$ and/or OR; with the proviso that when $X^3$ is a direct link or when $X^3$ is a one carbon atom unit, there are at least two carbon atoms between the COOH group and the nitrogen atom of E; whereby E is directly attached to $X^3$ via a carbon atom and is represented by a heterocyclic or a heteroaromatic 4 to 14 member ring, containing a nitrogen atom, which hetero cyclic or hetero aromatic group can be optionally substituted by one or more groups selected from $CF_3$, F, Cl, $NR'_2$, SR, $SO_2R$ and OR; such heterocyclic and/or heteroaromatic rings can contain from 1 to 3 additional hetero atoms chosen from oxygen, nitrogen and sulphur; such heterocyclic and/or heteroaromatic groups can be further substituted by one or more groups selected from $C_1$-$C_{10}$ linear, branched cyclic, aromatic, heterocyclic or heteroaromatic hydrocarbon groups which groups can be optionally substituted by $CF_3$, F, Cl, $NR'''_2$, SR", $SO_2R''$ and/or OR", wherein R, R', R" and R'" have the meaning recited above; such that the difference between the number of member atoms in the individual cycles of these heterocyclic or heteroaromatic rings minus the number of heteroatoms in the individual cycles of these heterocyclic or heteroaromatic rings is at least 2; provided that when $X^3$ is not a direct link, the carbon atom next to the carboxylic acid group is solely connected to hydrogen atoms and, at least, one carbon atom which carries the E group and when in iii, $X^3$ is only a one carbon unit between COOH and the E group then that carbon atom can be solely substituted by hydrogen and carbon atoms; and heating the reaction mixture at a temperature in the range of from 40° C. to 180° C. for a period of from 10 minutes to 30 hours.

The $P_4O_6$ can be represented by a substantially pure compound containing at least 85%, preferably more than 90%; more preferably at least 95% and in one particular execution at least 97% of the $P_4O_6$. While tetraphosphorus hexa oxide, suitable for use within the context of this invention, can be manufactured by any known technology, in preferred executions the hexa oxide can be prepared in accordance with the process disclosed in WO 2009/068636 and/or EP 08 168 898.8, entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. The hexa oxide so prepared is a pure product containing usually at least 97% of the oxide. The $P_4O_6$ so produced is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds. The reaction product can, in one preferred execution, be quenched to a temperature below 350 K.

The term "liquid $P_4O_6$" embraces, as spelled out, any state of the $P_4O_6$. However, it is presumed that the $P_4O_6$ participating in a reaction at a temperature of 45° C. to 180° C. is necessarily liquid or gaseous although solid species can, academically speaking, be used in the preparation of the reaction medium.

The sulfonic acid compound is selected from homogeneous and heterogeneous sulfonic and polysulfonic acids. While the sulfonic acid compound was found to beneficially mitigate the reaction and the one step formation of selected high purity phosphonic acid compounds in high yields starting from $P_4O_6$, the mechanism by virtue of which the sulfonic acid interferes is not well understood at this time; it can be said that the essential claim parameters are required to generate the by any standard unusually beneficial results.

Suitable homogeneous sulfonic acids have the formula:

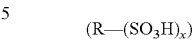

wherein R can be selected from $C_{1-24}$ hydrocarbon groups of linear, branched, cyclic or polycyclic configuration, possibly substituted by F and/or $CF_3$ groups, where x is 1 to 4, or $C_{6-14}$ aromatic or alkyl aromatic groups wherein the alkyl group can be $C_{6-20}$ where x is 1 to 3 for for monoaromatic systems and 1 to 4 for diaromatic and higher systems. R can also be represented by diphenylether or diphenylmethane or by $C_{6-20}$ alkyl diphenylmethane or $C_{6-20}$ alkyl diphenylether with x is 1 to 2.

Preferred heterogeneous sulfonic acids can be represented by species of discretionary selected subclasses as follows:

(1) sulfonic acids grafted onto resins comprising copolymers of styrene, ethylvinyl benzene and divinyl benzene functionalized so as to graft $SO_3H$ groups onto the aromatic groups can be used. These acidic resins can be used in different physical configurations such as in gel form, in a macro-reticulated configuration or supported onto a carrier material such as silica or carbon or carbon nanotubes. A known example of such resins is AMBERLYST 15 from Rohm and Haas. Other types of resins include perfluorinated resins carrying sulfonic acid groups. The fluorinated resins can be used as such or supported onto an inert material like silica or carbon or carbon nanotubes entrapped in a highly dispersed network of metal oxides and/or silica. NAFION is an example of such fluorinated resins. NAFION is a Trade Mark of the Du Pont Company. AMBERLYST 15 is a Trade Mark of the Rohm and Haas Company.

(2) sulfonic acids deposited on solids, having a lone pair of electrons, like silica, silica-alumina combinations, alumina, zeolites, silica, activated charcoal, sand and/or silica gel can be used as support for sulfonic acids, like methane sulfonic acid or para-toluene sulfonic acid. Solids, like zeolites, silica, or mesoporous silica e.g. MCM-41 or -48, or polymers like e.g. polysiloxanes can be functionalized by chemical grafting to thus yield sulfonic acid groups or precursors therefore. The functionalization can be introduced in various ways by direct grafting on the solid by e.g. reaction of the SiOH groups of the silica with chlorosulfonic acid; or can be attached to the solid by means of organic spacers which can be e.g. a perfluoro alkyl silane derivative. Sulfonic acid functionalized silica can also be prepared via a sol gel process, leading to e.g. a thiol functionalized silica, by co-condensation of $Si(OR)_4$ and e.g. 3-mercaptopropyl-tri-methoxy silane using either neutral or ionic templating methods with subsequent oxidation of the thiol to the corresponding sulfonic acid by e.g. $H_2O_2$. The functionalized solids can be used as is, i.e. in powder form, in the form of a zeolitic membrane, or in many other ways like in admixture with other polymers in membranes or in the form of solid extrudates or in a coating of e.g. a structural inorganic support e.g. monoliths of cordierite.

Homogeneous sulfonic acids are adapted to form a single liquid phase within the reaction medium under the reaction conditions. It is understood that the sulfonic acids which are insoluble in the reaction medium, and thus non-homogeneous, at ambient conditions e.g. 20° C., can become soluble at e.g. the reaction temperature and thus qualify as "homogeneous". The sulfonic acid may be recovered from the reaction medium by known techniques such as e.g. filtration of insoluble acids, or by other techniques routinely available such as ion exchange, nanofiltration or electrodialysis. The homogeneous nature of a sulfonic acid can be ascertained routinely by e.g. visible inspection of precipitation or phase separation properties.

The term heterogeneous means that the sulfonic acid is substantially insoluble in the reaction medium, at the reaction conditions. The insoluble nature of the acid can be ascertained routinely e.g. based on visible observation.

The sulfonic acid can, in one execution, be used in combination with water in a molar ratio $P_4O_6$:water of from 1:≤3 in particular 1:2 to 1:0.1. It is understood that the reaction can be conducted without the presence of water. The number of sulfonic acid equivalents of the heterogeneous sulfonic acid is based on acidity determinations.

Suitable homogeneous sulfonic acids can be solid at ambient temperature and shall preferably be used in combination with organic solvents which are inert in relation to the essential reaction partners. Suitable solvents are listed in the passage below.

The sulfonic is not, and cannot be equated to, a reactant in the context of the claimed technology. Actually, the sulfonic acid is, in fine, not chemically altered as a result of the claimed method although it may well be, probably is, that the sulfonic acid interferes in the formation of reaction intermediates. It is also noteworthy that the sulfonic acid can interfere with the amino carboxylic acid in the formation of a sulfonic acid salt. Thus it can be desirable when low levels of sulfonic acid are used, e.g. of from 1 to 2 equivalents per mole of aminocarboxylic acid, to use an aminocarboxylic acid salt as recited below.

The sulfonic acid can also be used together with an organic solvent. Generally organic solvents inert to the reagents can be used. This is understood for the man of the art as a solvent which does not react to any substantial degree with the reagents involved in the reaction. Typical examples of suitable solvents are as follows: anisole; fluorobenzene; chlorinated hydrocarbons such as chlorobenzene, tetrachloroethane, tetrachloroethylene; polar solvents like sulfolane, diglyme, glyme, diphenyl oxide, polyalkylene glycol derivatives with capped OH groups such as OR where R is a low alkyl or acyl group; aliphatic hydrocarbons such as hexane, heptane, cyclohexane; non-cyclic ethers like dibutyl ether, diisopropyl ether, and dipentyl ether; cyclic ethers like tetrahydrofuran and dioxane; aromatic hydrocarbons like toluene, xylene; organic acetates like ethyl acetate; organic nitriles like acetonitrile; silicon fluids like polymethylphenyl siloxane or mixtures thereof. Additionally co-diluents like e.g. phosphoric acid can optionally be added in molar ratio amino carboxylic acid:phosphoric acid of from 1:0.01 to 1:1. When using heterogeneous sulfonic acid, it is preferable to use polar solvents capable of solubilizing the reagents and at least in part the products formed. Suitable organic solvents shall be used in a molar ratio of aminocarboxylic acid:organic solvent of from 1:1 to 1:10, preferably 1:2 to 1:6. These organic solvents can also be used for preparing a $P_4O_6$ solution and an aminocarboxylic acid solution to be used in the reaction. Of course, in addition to these solvents, the liquid sulfonic acids or solid sulfonic acids, dissolved in a solvent e.g. as described above, can be used together with the other reactants in the sequence recited in the claims.

Preferred species of aminocarboxylic acid for use in this invention can be defined as follows. The term "cyclic" embraces -alkylene-cycloalkyl and -cycloalkyl-alkyl e.g. methylene cyclopentyl or methylcyclopentyl or methylmethylene cyclopentyl or combinations thereof. The terms "cyclic" or "aromatics" imply with respect to cyclic a structure of minimum 3 carbon atoms and with respect to aromatic a structure of at least 6 carbon atoms. The terms "polycyclic", "polyaromatic", "heteropolycyclic" and "heteropolyaromatic" embrace fused ring derivatives and rings attached to each other by a single bond and combinations thereof. Further, the terms "polycyclic" and "heteropolycyclic" also embrace bridged and spiro derivatives. With respect to i, $X^1$ can represent $C_{3-20}$ for cyclic and polycyclic groups and $C_{6-20}$ for aromatic or polyaromatic groups. The aromatic/polyaromatic groups can be represented by alkylaromatic (aryl), alkylene aromatic and alkylalkylene aromatic. Preferred $X^1$ species contain $C_{2-10}$ cyclic, linear or branched alkyl and aromatic groups. A, B are preferably selected from H and hydrocarbon groups having from $C_{1-10}$ in linear, branched, cyclic, aromatic, heterocyclic or heteroaromatic configuration; $X^2$ is preferably selected from $C_{1-6}$ hydrocarbon groups in linear, branched, cyclic, aromatic, heterocyclic or heteroaromatic configuration without any substituent. Preferred heterocycles D have from 5 to 6 members and contain from 1 to 2 heteroatoms, in addition to a nitrogen atom. D in ii can also be represented by a $C_{4-6}$ alkylimide or a $C_{8-12}$ aromatic imide. $X^3$ in iii is preferably selected from a direct link or a $C_{1-10}$ hydrocarbon group in linear, branched, cyclic, aromatic, heterocyclic or heteroaromatic configuration in particular from $C_{1-6}$ alkyl groups. Examples of suitable imide precursors are: succinic anhydride, glutamic anhydride and phthalic anhydride. Preferred E (iii) are structures having 5-10 member rings containing 1 to 3 heteroatoms in addition to a nitrogen atom.

Suitable and preferred aminocarboxylic acids herein include:
4-piperidine carboxylic acid (iii), also known as isonipecotic acid;
N,N-dimethyl-γ-aminobutyric acid (i);
N-methyl-γ-aminobutyric acid (i);
m-aminobenzoic acid (i); and
4-phthalimido-butyric acid (ii).

In particularly preferred executions herein, aminocarboxylic acids suitable for synthesizing highly desirable reaction products are as follows:

| Aminocarboxylic Acid; | Aminohydroxy Diphosphonic Acid |
|---|---|
| N,N-dimethyl β-alanine (i); | Olpadronic Acid |
| Imidazo[1,2-a]pyridine-3-acetic acid (iii); | Minodronic acid |
| 3-Pyridine Acetic acid (iii); | Risedronic acid |
| β-Alanine (i); | Pamidronic acid |
| Hexanoic acid, 6-amino- (i); | Neridronic acid |
| β-Alanine, N-methyl, N-pentyl (i); | Ibandronic acid |
| Butanoic acid, 4-amino- (i) | Alendronic acid. |
| Imidazoyl acetic acid (iii) | Zoledronic acid. |

The aminocarboxylic acid is usually solid at ambient conditions. When the aminocarboxylic acid is added to the sulfonic acid containing the $P_4O_6$ it can be added to the reaction medium as a solid, as a solution in the sulfonic acid or in an appropriate solvent or in admixture with the sulfonic acid and a solvent.

The aminocarboxylic acid can be used as such or as a salt to be added to the reaction medium, provided that the counterion is compatible with the $P_4O_6$. Examples of suitable ions include: mesylate; phosphate; iodide; bromide and chloride ions.

Inasmuch as the inventive method herein operates under exclusion of chlorides and LOOPS and yields high selectivity and purity products, the mother liquid can be very easily recycled to thus optimize the quantitative use and conversion of the reactants. The inventive method herein is particularly beneficial in that it allows, compared to the art, an easy and efficient recycling of the mother liquid after removal, in accordance with needs, of water and possibly solvents which have been used in the product isolation step.

The reaction product formed can be recovered in an appropriate manner by standard methods known to those skilled in the art. The reaction product can, for example, be isolated with the aid of known technologies. To illustrate one approach, one can start by adding water to the reaction medium to thus hydrolyze by heating, typically at a temperature in the range from 80 to 140° C., the reaction products formed to thus convert the reaction products to the free monomeric aminohydroxy diphosphonic acids which can, subsequently, be separated from the hydrolyzed reaction mixture by e.g. crystallization or precipitation by the addition of suitable co-solvent/diluent. The crystallized material or the precipitate can be isolated by e.g. filtration or centrifugation and further crystallized to meet e.g. pharmaceutical requirements. In another approach, one can recover the final product as a fully or partially neutralized acid salt. Suitable salt species preferentially include alkali and earth-alkali ions. The final salt products can be routinely isolated and purified e.g. by re-crystallization to thus yield the purified salt, possibly as a hydrate which meets pharmacopoeia requirements. Alternatively, the salts and their hydrates can be prepared from the isolated acid equivalents. The isolation and purification of the reaction products formed can require the use of routine measures well known to the notional artisan, such as treatment with activated carbon to remove residual traces of sulphur containing compounds.

The reaction in accordance with this invention is conducted in a manner routinely known in the domain of the technology. As illustrated in the experimental showings, the method can be conducted by combining the essential reaction partners and heating the reaction mixture to a temperature usually within the range of from 40° C. to 180° C., more preferably 60° to 160° C., in particular 80 to 140° C. The duration of the reaction at the selected temperatures is from 10 minutes to hours, preferably from 30 minutes to 20 hours, in particular from 1 hour to 18 hours. The upper temperature aims at preventing any substantial undue decomposition of the reactants, solvents or of intermediates formed in these reactions. It is understood and well known that the decomposition temperature of the reaction partners or solvents can vary depending upon physical parameters, such as pressure and the qualitative and quantitative parameters of the ingredients in the reaction mixture. The reaction can be conducted at ambient pressure. The duration of the reaction can vary from virtually instantaneous, e.g. 10 minutes, to an extended period of time e.g. 30 hours. This duration can include the gradual addition of the reactants. In one method set up, the $P_4O_6$ is added to the mixture of the aminocarboxylic acid and the sulfonic acid and the so formed mixture is heated to a temperature in the range of from 40° C. to 180° C. In another operational arrangement, the reaction can be conducted in a closed vessel.

In yet another arrangement with the aid of a heterogeneous catalyst, the reaction vessel containing the reaction mixture is kept, in the presence of the heterogeneous catalyst at the selected reaction temperature.

The foregoing process variables thus show that the reaction can be conducted by a variety of substantially complementary arrangements. The reaction can thus be conducted as a batch process by heating the initial reactants, usually the $P_4O_6$, the aminocarboxylic acid and the sulfonic acid in a closed vessel, possibly under autogeneous pressure built up to a temperature in the range of from e.g. 60° C. to 160 ° C. In a particularly preferred embodiment, the reaction is conducted in a closed vessel at a temperature in the range of from 80° C. to 140° C. for a period of from 30 minutes to 20 hours, in particular, from 1 hour to 18 hours. In yet another approach, the reaction is conducted as a continuous process, possibly under autogeneous pressure built up, whereby the reactants, usually a mixture, are continuously injected into the reaction zone at a temperature in the range from 40° C. to 180° C. The synthesis reaction can also be conducted continuously whereby the hydrolysis of the reaction product and the isolation/purification of the final diphosphonic acid product are done batchwise.

The technology of this invention is illustrated by means of examples as follows.

General procedure: In a three neck round bottom flask equipped with a mechanical stirrer, a reflux condenser and a dosing funnel are mixed an amino-acid, optionally water and a sulfonic acid with optionally a solvent under nitrogen atmosphere. $P_4O_6$ is added to this mixture at room temperature within 15 minutes. Alternatively, $P_4O_6$ is added to the sulfonic acid before the addition of the aminoacid. Molar ratios of the $P_4O_6$/water and amino acid/$P_4O_6$ as well as the sulfonic acid type, and ratios of sulfonic acid equivalents divided by moles of $P_4O_6$ and reaction conditions are indicated on Tables 1 and 2. The reaction mixture is then heated and maintained at a certain temperature for a given time before water addition so as to obtain a solution containing 30% w/w of water which is heated at 115° C. for 2 hours. $^{31}P$ NMR analysis of the crude product is carried out and the % w/w of the amino hydroxy diphosphonic acids calculated from the $^{31}P$ signals. Results are provided in Tables 1 and 2.

The reaction of the invention was been carried out in various conditions with the gamma-amino butyric acid or its phthalimido equivalent. Results are given in Table 1

TABLE 1

4-Amino-1-hydroxybutane-1,1-diphosphonic acid synthesis

| Exp | Mol. Ratio $P_4O_6$/$H_2O$ | Mol. Ratio Amino. Acid/$P_4O_6$ | Heating time and Temperature | Solvent system and ratios of sulfonic acid equivalents/ moles of $P_4O_6$ | $^{31}P$ NMR A-HADP# |
|---|---|---|---|---|---|
| 1 | 0.5 | 2 GABA* | 115° C. 2 hours | 12.5 MSA*** | 74.1% w/w |
| 2 | 1 | 2 GABA | 100° C. 2 hours | 12.5 MSA | 90.1% w/w |
| 3 | 2 | 2 GABA | 100° C. 2 hours | 12.5 MSA | 90.2% w/w |
| 4 | No $H_2O$ | 2 GABA | 100° C. 2 hours | 12.5 MSA | 91.9% w/w |

TABLE 1-continued

4-Amino-1-hydroxybutane-1,1-diphosphonic acid synthesis

| Exp | Mol. Ratio $P_4O_6/H_2O$ | Mol. Ratio Amino. Acid/$P_4O_6$ | Heating time and Temperature | Solvent system and ratios of sulfonic acid equivalents/ moles of $P_4O_6$ | $^{31}P$ NMR A-HADP[#] |
|---|---|---|---|---|---|
| 5 | No $H_2O$ | 2 GABA | 100° C. 6 hours | 12.5 MSA | 93.4% w/w |
| 6 | No $H_2O$ | 2 GABA | 100° C. 3 hours | 12.5 MSA | 92.8% w/w |
| 7 | No $H_2O$ | 2 GABA | 100° C. 2 hours | 8 MSA | 89.5% w/w |
| 8 | No $H_2O$ | 1.8 GABA | 100° C. 4 hours | 12.5 MSA | 90.2% w/w |
| 9 | No $H_2O$ | 2 GABA | 100° C. 2 hours | 12.5 ESA[+] | 87.9% w/w |
| 10 | No $H_2O$ | 2 GABA | 100° C. 2 hours | 8 Toluene 8.5 p-TSA[++] | 70.6% w/w |
| 11 | No $H_2O$ | 2 Pht-GABA** | 100° C. 2 hours | 8 Toluene 7.3 Amberlyst 15[+++] | 32% w/w |
| 12 | No $H_2O$ | 2 Pht-GABA | 100° C. 2 hours | 12.5 MSA | 67% w/w |

*GABA = gamma- amino butyric acid
**PhtGABA stands for 4-phthalimido butyric acid
***MSA stands for methane sulfonic acid
[+]ESA stands for ethane sulfonic acid
[++]p-TSA stands for para-toluene sulfonic acid
[+++]Amberlyst 15 is a sulfonic acid from Rohm and Haas Company, the number of equivalents is based on the number of sulfonic acid groups and the ratio of sulfonic acid equivalents/moles of $P_4O_6$ calculated there from
[#]A-HADP stands for amino alkyl hydroxy diphosphonic acid.

The reaction as described in the general procedure was repeated with other amino carboxylic acid in several conditions. Results and operating conditions are given in Table 2.

TABLE 2

Other amino-1-hydroxy-1,1-diphosphonic acid synthesis

| Exp. | Mol. Ratio $P_4O_6/H_2O$ | Mol. Ratio Amino. Acid/$P_4O_6$ | Heating time and Temperature | Solvent system and ratios of sulfonic acid equivalents/ moles of $P_4O_6$ | $^{31}P$ NMR A- HDP[###] |
|---|---|---|---|---|---|
| 13 | 0.5 | 2 β-Ala** | 100° C. 6 hours | 12.5 MSA | 54% w/w |
| 14 | 0.53 | 1.8 β-Ala | 100° C. 5 hours | 12.5 MSA | 53.2% w/w |
| 15 | No $H_2O$ | 2 β-Ala | 100° C. 2 hours | 19 MSA | 54.2% w/w |
| 16* | No $H_2O$ | 2 β-Ala | 100° C. 2 hours | 19 MSA | 59.3% w/w |
| 17 | No $H_2O$ | 2 β-Ala | 100° C. 4 hours | 19 MSA | 73.9% w/w |
| 18 | No $H_2O$ | 2 6-AHex[+] | 100° C. 2 hours | 12.5 MSA | 92.3% w/w |
| 19 | No $H_2O$ | 2 3-PyrAc[####] | 100° C. 3 hours | 20 MSA | 40.1% w/w |
| 20 | No $H_2O$ | 2 3-PyrAc | 100° C. 17 hours | 20 MSA | 78.7% w/w |
| 21 | No $H_2O$ | 2 DmGABA[++] | 100° C. 2 hours | 12.5 MSA | 93.4% w/w |
| 22 | No $H_2O$ | 2 MmGABA $MeSO_3H$ | 100° C. 2 hours | 12.5 MSA | 90.1% w/w |
| 23 | No $H_2O$ | 2 MmGABA | 100° C. 2 hours | 12.5 MSA | 92.8% w/w |
| 24 | No $H_2O$ | 2 4-PipCA*** | 100°c 2 hours | 12.5 MSA | 66% w/w |
| 25 | No $H_2O$ | 2 4-PipCA | 100° C. 6 hours | 16.3 MSA | 82.0% w/w |
| 26 | No $H_2O$ | 2 m-ABz[#] | 100° C. 2 hours | 12.5 MSA | 25.8% w/w |

*In experiment 16 $P_4O_6$ was added to MSA before addition of the β-alanine dissolved in MSA TABLE 2-continued Other amino-1-hydroxy-1,1-diphosphonic acid synthesis

| Exp. | Mol. Ratio $P_4O_6/H_2O$ | Mol. Ratio Amino. Acid/$P_4O_6$ | Heating time and Temperature | Solvent system and ratios of sulfonic acid equivalents/ moles of $P_4O_6$ | $^{31}$P NMR A- HDP## |
|------|--------------------------|----------------------------------|------------------------------|---------------------------------------------------------------------------|------------------------|

\*\*β-Ala stands for β-Alanine
\*\*\*4-PipCA stands for 4-Piperidine carboxylic acid
+6-AHex stands for 6-amino hexanoic acid
++DmGABA stands for N,N-dimethyl gamma-amino butyric acid
+++MmGABA MeSO$_3$H stands for N-monomethyl gamma-amino butyric acid as mesylate salt. MmGABA (Exp. 22) stands for N-monomethyl gamma-amino butyric acid
m-ABz stands for meta-aminobenzoic acid
A-HDP stands for amino hydroxy diphosphonic acid.
3-PyrAc stands for 3-pyridyl acetic acid The alendronic acid (4-amino-1-hydroxybutane-1,1-diphosphonic acid) was isolated from the crude reaction mixture of experiment 6 by addition of 2-propanol at 80° C. followed up by cooling to room temperature in 2 hours. The crystalline solid was separated by filtration, washed with 2-propanol and dried under reduced pressure. The product thus obtained (83% isolated yield) was chemically pure with only traces of 2-propanol and methanesulfonic acid. The mother liquor, after solvent and water evaporation, contained methane sulfonic acid, unconverted gamma-amino butyric acid, residual 4-amino-1-hydroxybutane-1,1-diphosphonic acid, some phosphorous acid and low level of phosphoric acid. This can be reused for alendronic acid synthesis after addition of reactants, in particular fresh gamma-amino butyric acid and $P_4O_6$.

The same reaction was carried out with amino carboxylic acids where the amino group is part of an aromatic ring or is a substituent of an aromatic ring in trifluoromethane sulfonic acid, according to the procedure given below.

Procedure: In a three neck round bottom flask fitted with a mechanical stirrer, a reflux condenser and a dosing funnel are mixed an amino carboxylic acid, trifluoromethane sulfonic acid (triflic acid) with optionally a solvent under nitrogen atmosphere. $P_4O_6$ is added to this mixture at room temperature in 10 minutes. Amino carboxylic acid/$P_4O_6$ and triflic acid/$P_4O_6$ molar ratios, as well as operating conditions are given in Table 3. After completion of $P_4O_6$ addition the reaction mixture is heated under stirring and kept at that temperature for a given time followed by addition of water in order to obtain a solution containing ca. 30% w/w of $H_2O$. This solution is further heated under stirring for 2 to 5 hours. $^{31}$P NMR analysis of the crude reaction mixture so obtained is carried out and the % w/w of amino hydroxy diphosphonic acid calculated there from. Results are given in Table 3.

TABLE 3

Amino-1-hydroxy-1,1- phosphonic acid synthesis from amino-aromatic carboxylic acids

| Exp. | Mol. Ratio amino acid/ $P_4O_6$ Amino acid | Heating time and Temperature | Solvent system and ratios of sulfonic acid equiv./moles of $P_4O_6$ | $^{31}$P NMR A- HDP# |
|------|---------------------------------------------|------------------------------|---------------------------------------------------------------------|------------------------|
| 1 | 2 IAA* | 100° C. 8 hours | 12 TfOH+ | 54.1% w/w |
| 2 | 1.33 IAA | 100° C. 16 hours | 8 TfOH | 48.1% w/w |
| 3 | 2 IAA | 100° C. 16 hours | 12 TfOH | 42.1% w/w |
| 4 | 2 NA | 100° C. 8 hours | 12 TfOH | 25.0% w/w |
| 5 | 2 m-ABz*** | 100° C. 7 hours | 8 TfOH | 61.0% w/w |

A- HDP stands for Amino Hydroxy di phosphonic acid;
*IAA stands for Imidazolyl Acetic Acid;
\*\*NA stands for Nicotinic Acid;
\*\*\*m-ABz stands for meta-Aminobenzoic acid;
+TfOH stands for triflic acid (trifluoromethane sulfonic acid)

COMPARATIVE EXAMPLE

Synthesis of (3-amino-1-hydroxypropylidene)-1,1-bisphosphonic Acid Derivative Following Patent DD 222030 A1

In a three-necked round-bottom flask equipped with a mechanical stirrer, a reflux condenser and a dosing funnel, 10.94 g of β-alanine were dispersed in 32 ml of 1,4-dioxane containing 2 mol/l of HCl. After 30 minutes of stirring, 7.0 ml of $P_4O_6$ were added at room temperature over 15 minutes. The heterogeneous mixture became stickier when $P_4O_6$ was added. There were clearly two layers, one liquid and another sticky, very viscous solid. The reacting medium was then heated at reflux under strong agitation. At 72° C. LOOPs formation started since the coloration of the solid and the liquid became yellow. Coloration darkened gradually with increasing temperature. When reflux was reached the sticky solid had become deep red and stirring became difficult because of solid accumulation in the flask. Reflux was maintained for 20 minutes then the mixture was cooled to 45° C. After the addition of 30 ml water, 15 ml of a 30% aqueous solution of $H_2O_2$ were slowly added to the reaction mixture. The red solid disappeared rapidly with the addition of hydrogen peroxide aqueous solution. This procedure is known to react LOOPs and convert them to phosphoric acid. Residual phosphorous acid is also converted to phosphoric acid under these conditions.

Temperature increased from 45 to 60° C. during this treatment. After cooling, the crude product was analysed by $^{31}$P NMR. Results show that the (3-amino-1-hydroxypropylidene)-1,1-bisphosphonic acid was formed with 42.9% w/w and that phosphoric acid was present at 45.9% w/w.

The aminohydroxy diphosphonic acid formed can generally be recovered and further purified in whatever form suits the application envisaged. As an example, the reaction products are usually recovered in the acid form and further purified in accordance with needs. The reaction products can, among others, be crystallized in various hydrate forms. The reaction products can also be neutralized, and further purified, to thus yield the phosphonate salts.

The invention claimed is:

1. A method for the manufacture of an aminohydroxy diphosphonic acid by combining a reaction mixture consisting essentially of the corresponding aminocarboxylic acid, $P_4O_6$ and a sulfonic acid and performing the steps as follows:
   a: adding the $P_4O_6$ to the solution of the aminocarboxylic acid in the sulfonic acid; or
   b: adding the $P_4O_6$ to the sulfonic acid followed by the addition of the amino carboxylic acid;
   wherein the sulfonic acid is selected from homogeneous and heterogeneous sulfonic and polysulfonic acids; and the amino carboxylic acid and the $P_4O_6$ are used in molar ratios of from 4:1 to 1:1 and the sulfonic acid is used in a level of from 1 to 30 equivalents per mol of amino carboxylic acid; and wherein the aminocarboxylic acid is selected from the group of:

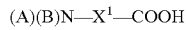   i wherein $X^1$ is such that there are at least two carbon units between COOH and N; $X^1$ can be represented by a hydrocarbon group selected from linear, branched, cyclic and aromatic species having from 2 to 20 carbon atoms, optionally substituted by one or more groups selected from $CF_3$, F, Cl, SR, $NR'_2$, $SO_2R$ and OR; A and B are independently selected from H, hydrocarbon groups having from 1 to 20 carbon atoms in branched, linear, cyclic, aromatic, heterocyclic or hetero aromatic configuration which can be substituted by OR, SR, $CF_3$, F, Cl, $NR'_2$, $SO_2R$ and/or R wherein R represents an alkyl group having from 1 to 12 carbon atoms in linear, branched, cyclic, aromatic, heterocyclic or heteroaromatic configuration which can be substituted by OR", SR", $CF_3$, F, Cl, $NR'''_2$ and/or $SO_2R''$ wherein R' is selected from R and hydrogen and can be selected independently; R" represents a hydrocarbon group having from 1 to 12 carbon atoms in linear, branched, cyclic, aromatic, heterocyclic or heteroaromatic configuration; R''' is selected from R" and hydrogen and R''' groups can be chosen independently; wherein the heterocyclic and heteroaromatic groups can contain from 1 to 4 heteroatoms independently selected from nitrogen, sulphur and oxygen; such that the difference between the number of member atoms in the individual cycles of these heterocyclic or heteroaromatic rings minus the number of heteroatoms in the individual cycles of these heterocyclic or heteroaromatic rings is at least 2; provided that the carbon atom next to the carboxylic acid group is solely connected to hydrogen and, at least, one carbon atom which carries the N(A)(B) group; when A is H, B can also be a COOT group whereby T is a $C_1$-$C_{10}$ alkyl group or a $C_6$-$C_{10}$ aromatic moiety;

D-$X^2$—COOH   ii wherein $X^2$ is at least one carbon atom between COOH and N; $X^2$ is a hydrocarbon group in linear, branched, cyclic or aromatic configuration having from 1 to 20 carbon atoms in said group, optionally substituted by $CF_3$, F, Cl, $NR'_2$, SR, $SO_2R$ and/or OR; with the proviso that when there is only one carbon atom between COOH and N then D represents a heteromonoaromatic group, in all other cases D represents a heteromonocyclic or heteromonoaromatic group containing at least one nitrogen atom directly attached to $X^2$, said heteromono cycle or heteromonoaromatic cycle being represented by a 4 to 8 member ring and containing from 1 to 3 additional hetero atoms chosen from nitrogen, oxygen and sulphur which cycle can be optionally substituted by one or more groups selected from $CF_3$, F, Cl, $NR'_2$, SR, $SO_2R$ and OR, which heteromonocycle or heteromonoaromatic cycle can be further substituted by one or more $C_1$-$C_{10}$ linear, branched, cyclic, aromatic, heterocyclic or heteroaromatic moieties, which can be substituted by one or more groups selected from $CF_3$, F, Cl, $NR'''_2$, SR", $SO_2R''$ and OR", wherein R, R', R" and R''' have the meaning recited above; which cyclic, heterocyclic, aromatic or heteroaromatic moieties, containing from 1 to 4 heteroatoms chosen from nitrogen, oxygen and sulphur can be fused onto the D group or attached to the D group by a single bond whereby in the cyclic structure fused onto the D group not more than four individual cycles are present; whereby the heterocyclic and heteroaromatic moieties, fused onto or attached to the D group by a single bond, and the D group itself are such that the difference between the number of member atoms in the individual cycles of these heterocyclic or heteroaromatic rings minus the number of heteroatoms in the individual cycles of these heterocyclic or heteroaromatic rings is at least 2; whereby the D group can also be represented by an imide derived from the $NH_2$ group attached to the $X^2$ moiety, formed by reaction with a cyclic anhydride; provided that the carbon atom next to the carboxylic acid group in ii is solely connected to hydrogen and, at least, one carbon atom which carries the D group and when in ii, $X^2$ is solely a one carbon unit between COOH and N in D, then that carbon atom can be solely substituted by hydrogen and carbon atoms; and

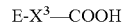   iii wherein $X^3$ is a direct link or a $C_1$-$C_{20}$ linear, branched, cyclic or aromatic hydrocarbon group, optionally substituted by $CF_3$, F, Cl, $NR'_2$, SR, $SO_2R$ and/or OR; with the proviso that when $X^3$ is a direct link or when $X^3$ is a one carbon atom unit, there are at least two carbon atoms between the COOH group and the nitrogen atom of E; whereby E is directly attached to $X^3$ via a carbon atom and is represented by a heterocyclic or a heteroaromatic 4 to 14 member ring, containing a nitrogen atom, which hetero cyclic or hetero aromatic group can be optionally substituted by one or more groups selected from $CF_3$, F, Cl, $NR'_2$, SR, $SO_2R$ and OR; such heterocyclic and/or heteroaromatic rings can contain from 1 to 3 additional hetero atoms chosen from oxygen, nitrogen and sulphur; such heterocyclic and/or heteroaromatic groups can be further substituted by one or more groups selected from $C_1$-$C_{10}$ linear, branched cyclic, aromatic, heterocyclic or heteroaromatic hydrocarbon groups which groups can be optionally substituted by $CF_3$, F, Cl, $NR'''_2$, SR", $SO_2R''$ and/or OR", wherein R, R', R" and R''' have the meaning recited above; such that the difference between the number of member atoms in the individual cycles of these heterocyclic or heteroaromatic rings minus the number of heteroatoms in the individual cycles of these heterocyclic or heteroaromatic rings is at least 2; provided that when $X^3$ is not a direct link, the carbon atom next to the carboxlic acid group is solely connected to hydrogen and, at least, one carbon atom which carries the E group and when in iii, $X^3$ is only a one carbon unit between COOH and the E group then that carbon atom can be solely substituted by hydrogen and carbon atoms; and c: heating the reaction mixture at a temperature in the range of from 40° C. to 180° C. for a period of from 10 minutes to 30 hours, wherein the reaction contains less than 400 ppm of chlorine expressed in relation to aminohydroxy diphosphonic acid (100%).

2. The method in accordance with claim 1 wherein $X^1$ is selected from $C_{2-10}$ cyclic, linear or branched alkyl and aromatic groups, and A and B are independently selected from H and $C_{1-10}$ hydrocarbon groups in linear, branched, cyclic, aromatic, heterocyclic or heteroaromatic configuration.

3. The method in accordance with claim 1 wherein $X^2$ is selected from $C_{1-6}$ hydrocarbon groups in linear, branched, cyclic, aromatic, heterocyclic or heteroaromatic configuration without any substituent.

4. The method in accordance with claim 1 wherein $X^3$ is selected from a direct link and $C_{1-10}$ hydrocarbon group in linear, branched, cyclic, aromatic, heterocyclic or heteroaromatic configuration.

5. The method in accordance with claim 1 wherein the sulfonic acid is used in a level of from 3 to 20 equivalents per mole of aminocarboxylic acid.

6. The method in accordance with claim 1 wherein the sulfonic acid is homogeneous and has the formula:

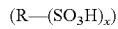

$(R-(SO_3H)_x)$ wherein R is selected from:
$C_{1-24}$ hydrocarbon groups of linear, branched, cyclic or polycyclic configuration, possibly substituted by F and/or $CF_3$ groups, where x is 1 to 4;
$C_{6-14}$ aromatic or alkyl aromatic groups wherein the alkyl group can be $C_{6-20}$ where x is 1 to 3 for monoaromatic systems and 1 to 4 for diaromatic and higher systems;
diphenyl ether or diphenylmethane;
$C_{6-20}$ alkyldiphenyl methane; and
$C_{6-20}$ alkyldiphenyl ether where x is 1 or 2.

7. The method in accordance with claim 1 wherein the sulfonic acid is heterogeneous, and is selected from:
sulfonic acids grafted onto resins comprising copolymers of styrene, ethylvinyl benzene and divinyl benzene functionalized so as to graft $SO_3$ groups onto the aromatic groups;
perfluorinated resins carrying sulfonic acid groups;
sulfonic acids deposited onto solids having a lone pair of electrons; and
polymers and inorganic solids functionalized by chemical grafting capable of yielding sulfonic acids.

8. The method in accordance with claim 1 wherein the $P_4O_6$ is manufactured by reacting oxygen and phosphorus in essentially stoichiometric amounts in a reaction unit at a temperature in the range of from 1600 to 2000 K with a reaction residence time from 0.5 to 30 seconds, followed by quenching the reaction product at a temperature below 700 K and refining the reaction product by distillation.

9. The method in accordance with claim 8 wherein the level of elementary phosphorus in the $P_4O_6$ is below 1000 ppm, expressed in relation to $P_4O_6$ (100%).

10. The method in accordance with claim 1, wherein the sulfonic acid is used in combination with water in a molar ratio of $P_4O_6$: water of from 1:2 to 1:0.1.

11. The method in accordance with claim 1 wherein the sulfonic acid is used together with an organic solvent selected from: anisole; fluorobenzene; chlorinated hydrocarbons; sulfolane; diglyme; glyme; diphenyl oxide; polyalkylene glycol; aliphatic hydrocarbons; non-cyclic ethers inluding dibutyl ether, diisopropyl ether, and dipentyl ether; cyclic ethers; aromatic hydrocarbons; organic acetates; organic nitriles; and silicon fluids; and wherein the organic solvent is used in a molar ratio of aminocarboxylic acid:organic solvent of from 1:1 to 1:10.

12. The method in accordance with claim 11 wherein a heterogeneous sulfonic acid is used in combination with a polar solvent selected from anisole, fluorobenzene, chlorinated hydrocarbons, organic acetates, organic nitriles, silicon fluids, sulfolane, diglyme, glyme, diphenyl oxide and polyalkylene glycol capped with OR groups where R is an alkyl or acyl group having from 1 to 8 carbon atoms.

13. The method in accordance with claim 1 wherein the aminocarboxylic acid is selected from:
4-piperidine carboxylic acid (iii);
N,N-dimethyl-γ-aminobutyric acid (i);
N-methyl-γ-aminobutyric acid (i);
m-aminobenzoic acid (i);
4-phthalimido-butyric acid (ii);
N,N-dimethyl β-alanine (i);
imidazo[1,2-a]pyridine-acetic acid (iii);
3-pyridine Acetic acid (iii);
β-alanine(i);
hexanoic acid, 6-amino- (i);
β-alanine, N-methyl, N-pentyl (i); and
butanoic acid, 4-amino- (i); and
imidazoyl acetic acid (iii).

* * * * *